United States Patent

Klanderman et al.

[11] 3,960,752
[45] June 1, 1976

[54] LIQUID CRYSTAL COMPOSITIONS

[75] Inventors: Bruce H. Klanderman; David P. Maier, both of Rochester, N.Y.

[73] Assignee: Eastman Kodak Company, Rochester, N.Y.

[22] Filed: Nov. 12, 1973

[21] Appl. No.: 415,196

Related U.S. Application Data

[63] Continuation-in-part of Ser. No. 300,008, Oct. 24, 1972, abandoned.

[52] U.S. Cl. .................. 252/299; 252/408; 350/150; 350/160 LC; 428/1
[51] Int. Cl.[2] .................. C09K 3/34; G02F 1/03; G02F 1/13; G02F 1/16
[58] Field of Search .................. 252/299, 408 LC; 350/160 LC; 350/150; 428/1

[56] References Cited

UNITED STATES PATENTS

| | | | |
|---|---|---|---|
| 3,540,796 | 11/1970 | Goldmacher et al. | 350/160 LC |
| 3,689,525 | 9/1972 | Scheurle et al. | 252/408 |
| 3,690,745 | 9/1972 | Jones | 252/299 |
| 3,769,313 | 10/1973 | Dietrich et al. | 252/408 |
| 3,772,210 | 11/1973 | Lodolini | 252/408 |
| 3,795,436 | 3/1974 | Boller et al. | 252/408 X |
| 3,796,479 | 3/1974 | Helfrich et al. | 252/408 LC |
| 3,815,972 | 6/1974 | Hsieh | 252/408 X |
| 3,826,757 | 7/1974 | Wong | 252/408 |
| 3,872,140 | 3/1975 | Klanderman et al. | 252/408 |
| 3,881,806 | 5/1975 | Suzuki | 252/299 |

FOREIGN PATENTS OR APPLICATIONS

| | | | |
|---|---|---|---|
| 2,306,739 | 8/1973 | Germany | 252/299 |
| 2,327,036 | 12/1973 | Germany | 252/299 |
| 2,024,269 | 12/1971 | Germany | 252/299 |
| 4,731,884 | 11/1972 | Japan | 252/299 |
| 4,731,882 | 11/1972 | Japan | 252/299 |
| 1,170,486 | 11/1969 | United Kingdom | 252/299 |

OTHER PUBLICATIONS

Boller, A., et al.; Proc. of the IEEE, vol. 60, pp. 1002–1003, (Aug., 1972).
USOL'TSEVA, V. A. et al.; Russian Chemical Reviews, Vol. 32, No. 9, pp. 495–509, (Sept., 1963).

Primary Examiner—Benjamin R. Padgett
Assistant Examiner—T. S. Gron
Attorney, Agent, or Firm—H. M Chapin

[57] ABSTRACT

In a nematic liquid crystal composition, the improvement wherein said composition comprises predominantly by weight a mixture of I. Compound I

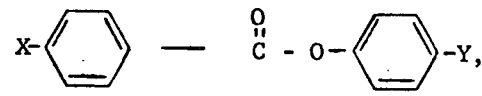

wherein one of X and Y is a strong electronegative group and the other of X and Y is $R^4$, $R^4O$-,

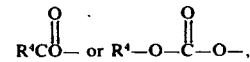

$R^4$ being an alkyl radical having 1 to 18 carbon atoms; with at least one member selected from the group consisting of:

II. a. a mixture resulting from the transiminization of at least one Schiff base of the formula:

Compound II

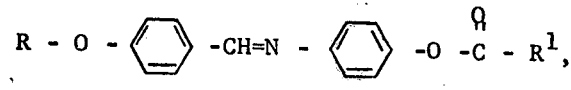

with at least one Schiff base of the formula:

Compound III

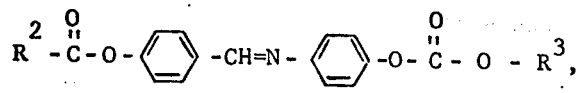

wherein R, $R^1$, $R^2$ and $R^3$ are alkyl radicals having 1 to 18 carbon atoms.

b. a mixture resulting from the transiminization of more than one type of Compound II with said at least one base of formula III, and c. a mixture resulting from the transiminization of more than one type of Compound III with said at least one Schiff base of formula II;

said composition being characterized by a Δε of about +1 or greater.

10 Claims, No Drawings

LIQUID CRYSTAL COMPOSITIONS

This application is a continuation-in-part of our abandonded application Ser. No. 300,008, filed Oct. 24, 1972, the disclosure of which is incorporated by reference herein.

This application relates to liquid crystal compositions, and more particularly, to nematic liquid crystal compositions useful in electro-optical devices.

Liquid crystal compositions are used in various electro-optical devices which involve the modulation of electromagnetic radiation, such as light valves and transmissive or reflective optical display devices. Such light valves are controlled by an electric field and operate when the nematic liquid crystal material is in its mesomorphic state.

Mesomorphism has been described as a state of matter with molecular order between that of a crystalline solid and a normal liquid. Crystalline solids are characterized by a non-random distribution of the molecules and a three-dimensional order in the location of the individual molecules within the crystal lattice. Normal liquids generally show isotropic behavior, for example, to light, due to the fact that the molecules of the liquid are randomly oriented.

In the mesomorphic state of mesophase of liquid crystal compositions, which are comprised of rod-shaped molecules, the directional arrangement of at least a part of the molecules is non-random. Among the various types of liquid crystal compositions, nematic liquid crystals are characterized by the fact that the long axes of the molecules maintain a parallel or nearly parallel arrangement to each other such that a one-dimensional order exists. Nematic liquid crystal compositions are usually characterized by a turbid appearance.

The mesophases of liquid crystal compositions exist over a temperature range which is dependent on the specific nature of the composition and molecular structure. Below this range the compositions become crystalline solids and above this range the preferred directional alignment of the molecules is destroyed and a normal liquid having isotropic behavior results. Both of these phase changes are characterized by sharp transition points.

In the mesomorphic state, the anisotropic properties of the individual molecules are conferred upon the bulk material. In regard to dielectric properties, the dielectric constant parallel to the long axis of the molecules can be larger or smaller than the dielectric constant perpendicular to the long axis of the molecules.

One of the main electro-optical applications of some nematic liquid crystal compositions is based on the fact that the molecules of the nematic liquid crystals exhibit a high dielectric constant along their long axis, because the dipole moment parallel to the long axis of the molecules is greater than the dipole moment in the perpendicular direction, and the molecules are said to possess positive dielectric anisotropy.

The molecules can be aligned uniaxially parallel to a surface giving a transparent appearance, and when an external magnetic or electric field is applied above a threshold value perpendicular to the surface orientation of these molecules, they will orient parallel to this field. In either aligned state, that is, aligned uniaxially parallel to the surface or aligned with the field, the nematic crystal compositions are birefringent. This electro-optical phenomenon is a field effect.

The nematic mesophase of the specific liquid crystalline compound is generally restricted within a narrow temperature range. However, it is possible to broaden the temperature range of the mesophase of the nematic liquid crystal composition by utilizing mixtures of different species of nematic liquid crystals.

Where the use of a liquid crystal composition is dependent on a field effect, the temperature of the device must be within the temperature limits of the mesophase. However, under certain circumstances liquid crystal mixtures can operate for several degrees below the solid crystal-mesomorphic transition temperature if the liquid crystal mixture is in a super-cooled state.

Many prior art liquid crystal compositions, such as disclosed in U.S. Pat. No. 3,540,796, have a relatively high solid crystal-mesomorphic transition point. In the case of such prior art liquid crystal compositions, heat must be applied to keep the compositions in the mesophase below about room temperature. Other prior art liquid crystal compositions have a relatively poor stability of the liquid crystal molecules. Examples of such relatively unstable liquid crystal compositions are disclosed in Applied Physics Letter 18 (14) page 127 (1971) by M. Schadt and W. Helfrich. This publication discloses liquid crystals formed by cyano group substituted Schiff bases whose azomethine linkage is easily split.

Other liquid crystal compositions of the prior art such as those disclosed in U.S. Pat. No. 3,540,796 show mixtures of Schiff bases with alkoxy and acyloxy substituents. Such prior art liquid crystals show a negative dielectric anisotropy.

German Offenlegungsschrift No. 2,017,727 discloses liquid crystal compositions with two component mixtures of Schiff bases with alkyl and acyloxy substituents. These liquid crystal compositions like the compositions mentioned above show a negative dielectric anisotropy. However, such liquid crystal compositions have relatively low hydrolytic stability.

The present invention relates to nematic liquid crystal compositions comprising predominantly (based on the weight of such compositions) a mixture of at least one compound of the formula:

Compound I

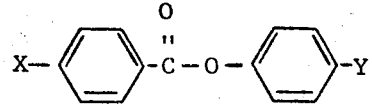

wherein one of X and Y is an electronegative group, advantageously CN, and the other of X and Y is $R^4$, $R^4-O-$,

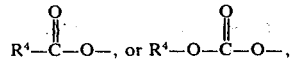

$R^4$ being an alkyl radical having 1 to 18 carbon atoms, advantageously $-OC_5H_{11}$; with at least one member selected from the group consisting of: a mixture resulting from the transiminization reaction of at least one Schiff base compound of the formula:

Compound II

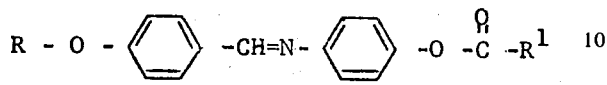

where R and R[1] are alkyl radicals of 1 to 18 carbon atoms, with at least one Schiff base compound of the formula:

Compound III

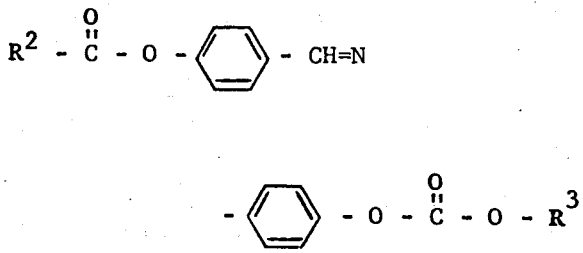

wherein R[2] and R[3] are alkyl radicals of 1 to 18 carbon atoms; as well as compositions comprising predominantly (based on the weight of such compositions) Compound I and the transiminization product of more than one type of Compound II or Compound III. As used herein, the term "more than one type" of Compound II or Compound III refers to compounds having the general formulas of Compound II or Compound III but having different length carbon chains for at least one of the alkyl radicals.

By transiminization is meant the reversible formation and cleavage of the imine linkages of at least two Schiff bases in which the aldehyde and amine portions interchange with one another. Referring to Compounds II and III, for the purposes of the above definition, the portion of each molecule extending from the left end to and including the —CH= represents the aldehyde portion of the molecule; and the portion of each molecule extending from the right end to and including the =N— represents the amine portion of the molecule.

The electro-optical devices using nematic liquid crystal compositions of the invention represent technical applications of the twisted nematic field effect. The term "twisted nematic field effect" within the context of this application is intended to convey the meaning that the nematic liquid crystal compositions of the invention are characterized by a positive dielectric anisotropy and a high electrical resistivity (generally at least about $1 \times 10^{10}$ ohm-cm). The twisted nematic field can be obtained with the nematic liquid crystal compositions of the invention under the following conditions:

1. a uniaxial, parallel orientation of the liquid crystalline molecules with respect to an electrode surface,
2. two uniaxially aligned electrode surfaces of the nematic liquid crystal molecules being twisted 90° with respect to each other, and
3. a pair of optical polarizers sandwiching the electrode surfaces and whose relative orientation to each other determines whether the optical device is transparent or opaque under the influence of an electric field, i.e., polarizers oriented parallel to each other will give an opaque "off" state (no electric field) and a transparent "on" state.

The nematic liquid crystal compositions of the invention are further characterized by having a mesophase temperature range that is at least about 100° centigrade in extent and that encompasses room temperature (e.g. a range of 0°C to 100°C, or of 10°C to 120°C, or of −10°C to 105°C and so forth). Such compositions can thus be utilized at ambient temperatures without additional heating, and they do not require the careful temperature control needed for compositions having narrower mesophase temperature ranges. In addition, the present nematic liquid crystal compositions have relatively good stability to hydrolytic cleavage.

The nematic liquid crystal compositions of the invention have a positive dielectric anisotropy which makes the compositions useful in display devices which are based on a field effect. In this mode the liquid crystal is oriented parallel to an applied electric field but perpendicular to the direction of the field when the field is not present. No conductivity is necessary or desirable for this mode.

The broad mesomorphic range for the liquid crystal compositions having a positive dielectric anisotropy can be obtained by adding a relatively small amount of a nematic liquid crystal of formula I which has a positive dielectric anisotropy of sufficient magnitude to a broad range nematic mixture possessing a negative dielectric anisotropy of relatively small magnitude yet which can be sufficiently large for dynamic scattering. Small quantities of the added nematic material possessing a large positive dielectric anisotropy will not significantly alter the temperature range of the final mixture although the final anisotropy will be of sufficient magnitude to permit its use in a field effect device.

Compound I is a phenyl benzoate possessing a positive dielectric anisotropy ($\Delta\epsilon$) of such magnitude ($\Delta\epsilon$ greater than +5 at 25°C) that a mixture with material possessing a negative dielectric anisotropy will have a resulting dielectric anisotropy ($\Delta\epsilon$) of about +1 or greater. Phenyl benzoates containing a strong electronegative group in a para position will possess a large positive dielectric anisotropy. A cyano group (—CN) is preferably used as the electronegative group. Other suitable electronegative groups include: —NO$_2$, —CF$_3$, and —SO$_2$— lower alkyl (wherein the alkyl radical has 1 to 8 carbon atoms), or comparable electronegative groups. R[4] of Compound I is an alkyl radical suitably having 1 to 18 carbon atoms, more generally 1 to 12 carbon atoms, and preferably 1 to 8 carbon atoms. Examples of Compound I include 4-cyanophenyl-4-acetyloxy benzoate, 4-cyanophenyl-4-pentyloxy benzoate, 4-stearoyloxyphenyl-4-cyanobenzoate and 4-pentyloxyphenyl-4-cyanobenzoate.

R and R[1] of Compound II are alkyl radicals, suitably having 1 to 18 carbon atoms, more generally 1 to 12 carbon atoms, and preferably 1 to 8 carbon atoms. R and R[1] can be the same or different, but preferably R and $R^1$ are different. Advantageously R is $CH_3$ or $C_4H_9$, and R' is $C_3H_7$ or $C_2H_5$. Examples of Compound II include p-[(p-methoxybenzylidene)amino]phenyl stearate, p-[(p-methoxybenzylidene)amino] phenyl butyrate, p[(p-butoxybenzylidene)amino] phenyl propionate, and p[(p-octadecoxybenzylidene)-amino] phenyl acetate.

$R^2$ and $R^3$ of Compound III are alkyl radicals suitably having 1 to 18 carbon atoms, more generally 1 to 12 carbon atoms, and preferably 1 to 8 carbon atoms. $R^2$ and $R^3$ are different. Advantageously $R^2$ is $C_4H_9$ and $R^3$ is $C_5H_{11}$. Examples of Compound III include N-(p-acetyloxybenzylidene)-p-octadecoxy-carbonyloxyaniline, N-(p-octadecanoyloxybenzylidene)-p-methoxycarbonyloxyaniline, N-(p-valeryloxybenzylidene)-p-pentoxycarbonyloxyaniline and N-(p-valeryloxybenzylidene)-p-methoxycarbonyloxyaniline.

Compound II and Compound III are Schiff bases, which are compounds which contain an azomethine moiety —CH=N— (also known as an imine linkage) having a carbon atom directly attached at either end of the moiety.

The compounds used in the nematic liquid crystal compositions of the invention can be prepared by conventional methods and purified by careful recrystallization until a constant and reversible mesomorphic range is attained. Impurities that would impart an excessive amount of conductivity are removed. The extraneous color of each compound is reduced to a minimum to achieve a mixture with a minimum of extraneous color.

The liquid crystal compositions of this invention include the transiminization (interconversion) products of Compounds II and III. This transiminization takes place at the azomethine linkages of the Schiff bases, Compounds II and III, and gives a mixture of all possible Schiff bases containing the ester, carbonate and ether components of the original Schiff bases. The transiminization reaction can be effected by heating a mixture of Compounds II and III, or such a mixture containing more than one type of either Compound II or Compound III. Typically the molar ratios of Compound II to Compound III, or different types of either Compound II or Compound III, before transiminization vary from about 5/1–1/5, with about 3 molar parts of Compound II to 1 molar part of Compound III being preferred. Compound I can be added either before or after the transiminization reaction as Compound I is not a Schiff base and does not take part in the transiminization reaction. Mixtures of more than one type of Compound I can be utilized. Typically the amount of Compound I based on the nematic liquid crystal composition varies from about 5 to 45 mole percent.

The nematic liquid crystal compositions of the invention comprise predominantly by weight a mixture of Compound I and the described transiminization Schiff base mixtures, although such compositions more generally comprise at least about 80 percent by weight of, and preferably consist essentially of, such Compound I and Schiff base mixtures.

The components of the transiminization mixture are heated to effect transiminization. A useful temperature range for heating the mixture is from about 50° to about 120°C. Higher temperatures can be used in order to shorten the reaction time. However, the temperature should not exceed the temperature of decomposition of the ingredients or the reaction products. Typically, the reaction mixture is heated to a suitable elevated temperature for a period of time which can vary from several minutes to several days. Reaction time varies with such factors as purity of materials, reaction temperatures, amount of reactants and the presence of catalysts.

The transiminization process can be conducted in the presence of a catalyst. In some cases, the catalyst substantially increases the rate of transiminization. Typical catalysts include alkylamine salts (e.g. triethylamine hydrochloride), ammonium chloride, sodium acetate, ammonium acetate, and the like. In addition, small amounts of water can facilitate the reaction. After the transiminization process, the mixture can thereafter be "worked-up" or purified in accordance with usual chemical practice to remove impurities, including catalyst materials, that might adversely affect the desired resistivity of the mixture. Resistivities of at least about $1 \times 10^{10}$ ohm-cm are preferred.

The following examples are included for a further understanding of the invention.

EXAMPLE I

A mixture of 2 molar parts of p-[(p-methoxybenzylidene)amino]phenyl butyrate, 1 molar part of p [(p-butoxybenzylidene) amino]-phenyl propionate and 1 molar part of N-(p-valeryloxybenzylidene)-p-pentoxycarbonyloxyaniline (respectively compounds numbers 1, 2 and 3 below) were combined with 0.4% by weight of purified triethylamine hydrochloride as a transiminization catalyst and heated at 80°C for 4 hours. The reaction mixture was diluted with a large amount of benzene and then filtered twice through a fine sintered-glass funnel. The benzene was removed under vacuum. The resulting composition had a nematic range from −5° to 103°C, and Δε of −1.668. $\Delta\epsilon = \epsilon_{||} - \epsilon_\perp$ $\epsilon_{||}$ and $\epsilon_\perp$ represent values for the dielectric constant ($\epsilon$) when the long axis of the nematic crystal is parallel ( || ) or perpendicular ( ⊥ ) to the electric field. Δε is the dielectric anisotropy. The resulting composition was a nine-component mixture consisting essentially of the following compounds:

| | Compound | Area % |
|---|---|---|
| 1. | $CH_3O-\phi-CH=N-\phi-OC(=O)-C_3H_7$ | 24 |
| 2. | $C_4H_9O-\phi-CH=N-\phi-OC(=O)-C_2H_5$ | 9 |
| 3. | $C_4H_9C(=O)-O-\phi-CH=N-\phi-OCO-C_5H_{11}$ | 5 |

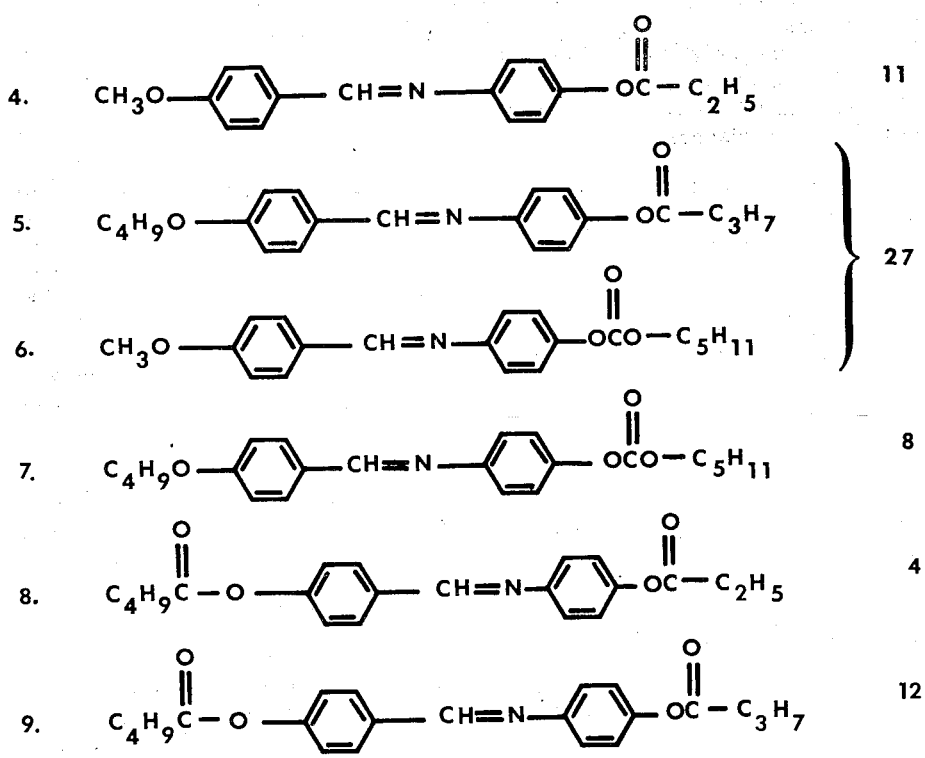

*These data were obtained with a vapor phase chromatographic unit. The area percent for each peak on the resulting graph was then determined. The identity of each peak was established with a gas phase chromatograph-mass spectrometer unit.

To a portion of the mixture was added 10 mole percent of 4-cyanophenyl-4-pentoxybenzoate ($\Delta\epsilon = +$ 16.2 at 72°C; approximately 29 ± 3 at 25°C) (8.5% by weight of the composition). The resulting nematic liquid crystal composition has a mesophase temperature range of −8°C to 97°C, a $\Delta\epsilon$ of + 1.567 and a resistivity of about 2 × $10^{10}$ ohm-cm. When the nematic liquid crystal composition is placed between two glass plates having transparent conductive surfaces that were rubbed with cotton cloth and oriented 90° to each other with respect to the direction of rubbing, sandwiched between two optical polarizers at 25°C and $10^4$ volts/cm. of direct current electric field is applied, a twisted nematic field effect is observed. The prepared nematic liquid crystal composition has substantial stability to hydrolytic cleavage.

EXAMPLE II

To a second portion of the nine-component mixture of Example I was added 20 mole percent of 4-cyanophenyl-4-pentoxybenzoate ($\Delta\epsilon = +$ 16.2 at 72°C; approximately 29 ± 3 at 25°C) (15.7% by weight of the composition). The resulting nematic liquid crystal composition has a mesophase temperature range of −1° to 101°C a resistivity of about 1 × $10^{10}$ ohm-cm and displays a field effect when placed in an electric field between transparent conductive surfaces as described in Example I.

EXAMPLE III

To a third portion of the nine-component mixture of Example I was added 20 mole percent of 4-pentoxyphenyl-4-cyanobenzoate ($\Delta\epsilon = +4.6$ at 88°C; approximately +9 ± 1 at 25°C) (15.7 % by weight of the composition). The resulting nematic liquid crystal composition had a mesophase temperature range of −3° to 94°C, a resistivity of about 1 × $10^{10}$ ohm-cm and displays a field effect when placed in an electric field between transparent conductive surfaces as described in Example I.

As used herein: —$CH_3$ refers to a methyl radical, —$C_2H_5$ refers to an ethyl radical, —$C_3H_7$ refers to a n-propyl radical, —$C_4H_9$ refers to a n-butyl radical and —$C_5H_{11}$ refers to a n-pentyl radical.

Reference is made to three other U.S. patent applications which are assigned to Eastman Kodak Company like the present application, and which relate to liquid crystals:

A.

Ser. No. 300,007
Filed: Oct. 24, 1972
Inventors: Bruce H. Klanderman, Richard T. Klingbiel
Title: Liquid Crystal Compositions
Abandoned in favor of a continuation-in-part Ser. No. 415,197, filed Nov. 12, 1973.

Describes and claims a nematic liquid crystal composition comprising a transiminized mixture of compounds II and III of the present invention, without compound I.

The compositions of Ser. No. 415,197 are characterized by a negative dielectric anisotropy which makes the compositions useful in display devices which are based on a dynamic scattering effect.

B.

Ser. No. 331,438
Filed: Feb. 12, 1973
Inventors: Bruce H. Klanderman and T. R. Criswell
Title: Liquid Crystalline Compositions And Method
U.S. Pat. No. 3,872,140, granted Mar. 18, 1975.

Describes and claims a method for forming mixtures of Schiff bases wherein at least two different Schiff bases are mixed together and heated in the presence of a catalyst to effect transminization.

C.

Serial No. 388,516
Filed: August 15, 1973
Inventors: James P. VanMeter, Bruce H. Klanderman
Title: Liquid Crystalline Compounds And Compositions. Patent No. 3,915,883, granted October 28, 1975.

Describes and claims an electro-optical cell comprising a film of liquid crystalline compounds which are substituted phenyl p-benzoyloxy-benzoates and also claims the substituted phenyl p-benzoyloxybenzoate compounds.

The invention has been described in detail with particular reference to preferred embodiments thereof, but it will be understood that variations and modifications can be effected within the spirit and scope of the invention.

We claim:
1. A nematic liquid crystal composition comprising a mixture of:

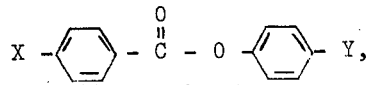

wherein one of X and Y is a strong electronegative group and the other of X and Y is $R^4$, $R^4O-$,

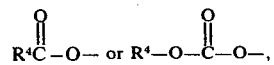

$R^4$ being an alkyl radical having 1 to 18 carbon atoms; with

II. a mixture resulting from the transiminization reaction of at least one Schiff base of the formula

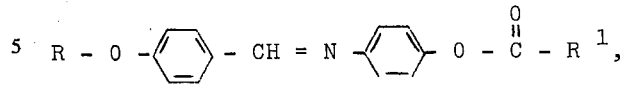

with at least one Schiff base of the formula:

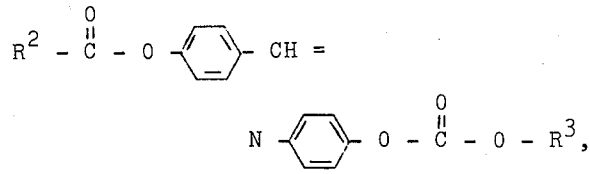

wherein R, $R^1$, $R^2$, and $R^3$ are alkyl radicals having 1 to 18 carbon atoms, said composition being characterized by a positive dielectric anisotropy $\Delta\epsilon$ of about +1 or greater.

2. A nematic liquid crystal composition according to claim 1 wherein Compound I comprises about 5 to 45 mole percent of said composition, and Compound II and Compound III are subjected to transiminization at a molar ratio of about 5/1 to 1/5.

3. A nematic liquid crystal composition according to claim 1 wherein R is $-CH_3$ or $-C_4H_9$, $R^1$ is $-C_3H_7$ or $-C_2H_5$, $R^2$ is $-C_4H_9$, $R^3$ is $-C_5H_{11}$, one of X and Y is $-CN$ and the other of X and Y is $-OC_5H_{11}$.

4. A nematic liquid crystal composition according to claim 1 wherein R, $R^1$, $R^2$, $R^3$, and $R^4$ are alkyl radicals of 1 to 8 carbon atoms.

5. A nematic liquid crystal composition according to claim 1 wherein either X or Y is $-CN$.

6. A nematic liquid crystal composition according to claim 1 consisting essentially of a mixture of:

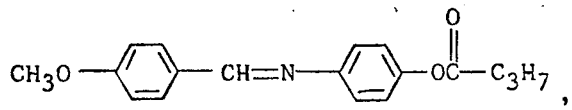

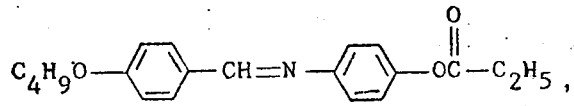

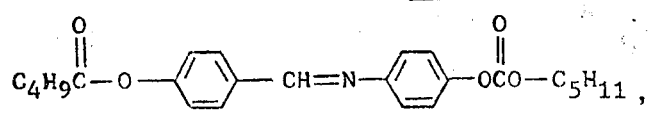

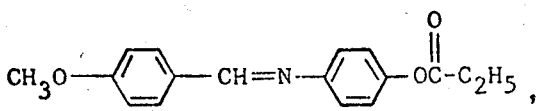

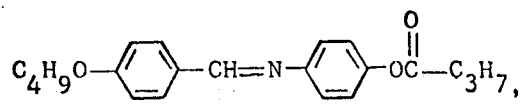

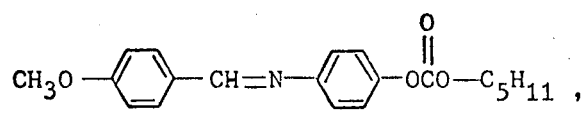

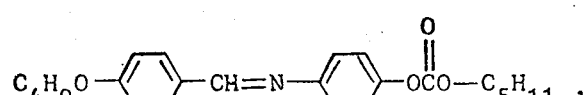

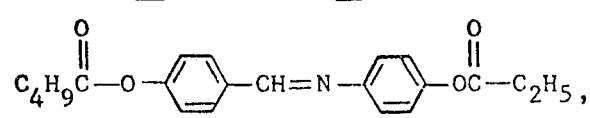

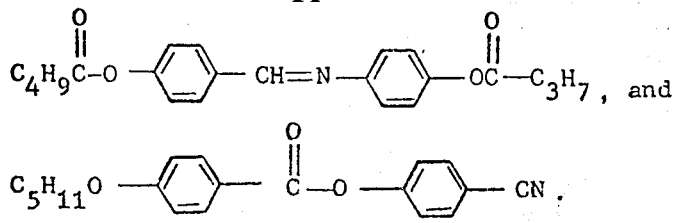

7. A nematic liquid crystal composition according to claim 1 consisting essentially of a mixture of:

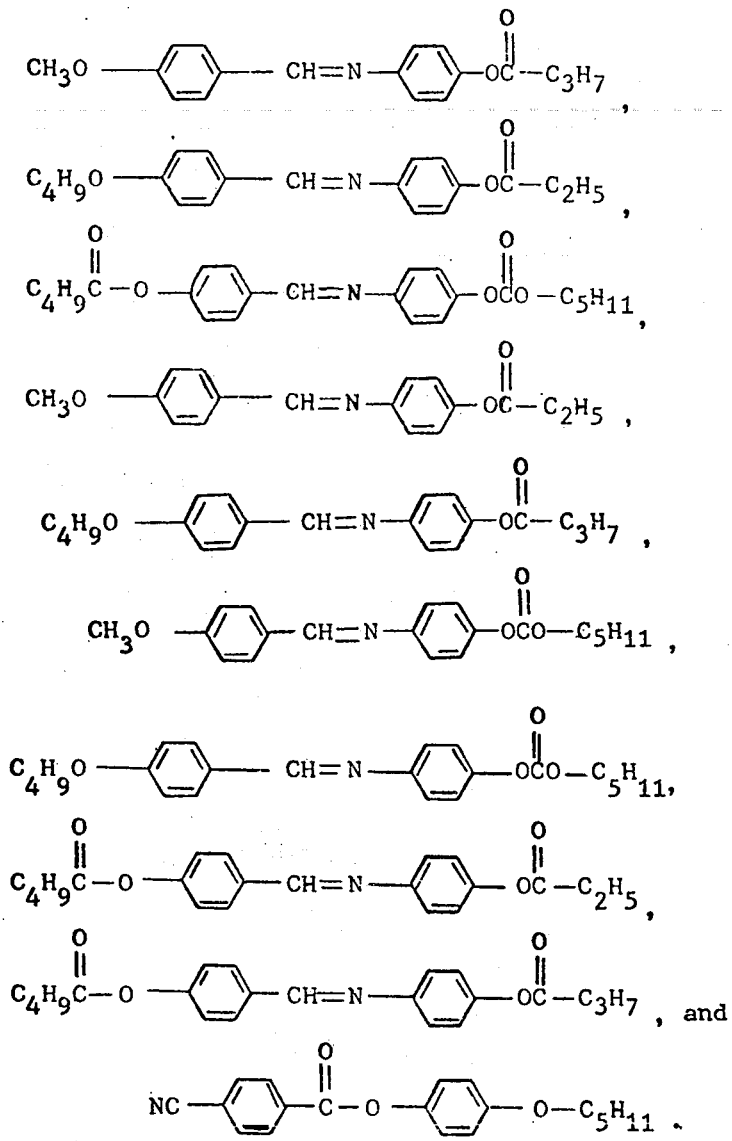

8. A nematic liquid crystal composition in accordance with claim 1 wherein said electronegative group in Compound I is selected from the group consisting of —CN, —NO$_2$, —CF$_3$, and —SO$_2$— lower alkyl (wherein the alkyl is C$_1$–C$_8$).

9. A nematic liquid crystal composition in accordance with claim 1, said mixture resulting from the transiminization of more than one type of Schiff base of the formula of Compound II with said at least one Schiff base of the formula of Compound III.

10. A nematic liquid crystal composition in accordance with claim 1, said mixture resulting from the transiminization of more than one type of Schiff base of the formula of Compound III with said at least one Schiff base of the formula of Compound II.

* * * * *

UNITED STATES PATENT OFFICE
CERTIFICATE OF CORRECTION

PATENT NO. : 3,960,752
DATED : June 1, 1976
INVENTOR(S) : Bruce H. Klanderman and David P. Maier It is certified that error appears in the above-identified patent and that said Letters Patent are hereby corrected as shown below:

In abstract, column 2, paragraph (b.), line 3, change "one base" to --one Schiff base--

Column 1, line 1 of paragraph 5, after "state" change "of" to --or--

Column 3, line 15, change "where" to --wherein--

Column 5, line 10, after "atoms." the following sentence should read as follows: $--R^2$ and $R^3$ can be the same or different, but preferably $R^2$ and $R^3$ are different.--

Column 9, claim 1, after "mixture of:" insert and indent --I. Compound I,--

Column 10, claim 1, after line 2, insert and indent -- Compound II--

Column 10, claim 1, after line that reads "with at least one Schiff base of the formula:", inset and indent --Compound III--

Signed and Sealed this

Twenty-sixth Day of October 1976

[SEAL]

Attest:

RUTH C. MASON
Attesting Officer

C. MARSHALL DANN
Commissioner of Patents and Trademarks